(12) United States Patent
Li et al.

(10) Patent No.: US 10,143,625 B2
(45) Date of Patent: Dec. 4, 2018

(54) PHARMACEUTICAL RECONSTITUTION

(71) Applicant: Recon Therapeutics, Inc., Brookline, MA (US)

(72) Inventors: Xiang Li, Ypsilanti, MI (US); Benjamin E. Maimon, Westfield, NJ (US); Ho-Jun Suk, Cambridge, MA (US)

(73) Assignee: Recon Therapeutics, Inc., Brookline, MA (US)

( * ) Notice: Subject to any disclaimer, the term of this patent is extended or adjusted under 35 U.S.C. 154(b) by 312 days.

(21) Appl. No.: 14/660,639

(22) Filed: Mar. 17, 2015

(65) Prior Publication Data

US 2016/0271018 A1 Sep. 22, 2016

(51) Int. Cl.
*A61M 5/178* (2006.01)
*A61J 1/20* (2006.01)
*A61J 1/06* (2006.01)

(52) U.S. Cl.
CPC .............. *A61J 1/2096* (2013.01); *A61J 1/062* (2013.01); *A61M 5/1782* (2013.01)

(58) Field of Classification Search
CPC .............. A61M 5/3294; A61M 5/2096; A61M 5/31501; A61M 5/2066; A61M 5/284; A61J 1/0625; A61J 1/2096; A61J 1/2089
See application file for complete search history.

(56) References Cited

U.S. PATENT DOCUMENTS

| | | | |
|---|---|---|---|
| 1,625,035 | A | 4/1927 | Lilly |
| 3,542,023 | A | 11/1970 | Ogle |
| 3,739,947 | A | 6/1973 | Baumann et al. |

(Continued)

FOREIGN PATENT DOCUMENTS

| | | |
|---|---|---|
| CA | 2745320 | 1/2013 |
| CA | 2783251 | 1/2014 |

(Continued)

OTHER PUBLICATIONS

ISA, "PCT Application No. PCT/US16/22782 International Search Report and Written Opinion dated Jun. 10, 2016", 14 pages.

(Continued)

*Primary Examiner* — Bhisma Mehta
*Assistant Examiner* — Matthew A Engel
(74) *Attorney, Agent, or Firm* — Strategic Patents, P.C.

(57) ABSTRACT

A device is disclosed for reconstitution and delivery of an injectable pharmaceutical. A pharmaceutical composition such as a lyophilized drug is provided in a pressurizable fluid reservoir with a pierceable seal. A diluent may be separately provided in a syringe with a needle. When the needle is driven through the seal and the plunger is actuated, fluid from the barrel of the syringe flows into the pressurizable fluid reservoir to simultaneously pressurize the reservoir and mix the diluent with the drug. Pressurized in this manner, the reservoir can then automatically and without further user intervention push the mixture back through the needle and into the barrel of the syringe, further mixing the composition and displacing the plunger to fill the barrel with the reconstituted drug. The needle and syringe can then be detached from the reservoir with the reconstituted drug contained in the barrel and ready for injection.

12 Claims, 6 Drawing Sheets

(56) References Cited

U.S. PATENT DOCUMENTS

| | | | |
|---|---|---|---|
| 4,243,080 A | 1/1981 | Penny et al. | |
| 4,286,389 A | 9/1981 | Ogle | |
| 4,516,967 A | 5/1985 | Kopfer et al. | |
| 4,717,384 A | 1/1988 | Waldeisen et al. | |
| 4,767,008 A | 8/1988 | Warnecke et al. | |
| 4,997,430 A | 3/1991 | Van der Heiden et al. | |
| 5,281,198 A | 1/1994 | Haber et al. | |
| 5,433,330 A | 7/1995 | Thomas et al. | |
| 5,779,668 A | 7/1998 | Grabenkort | |
| 6,341,718 B1 | 1/2002 | Schilthuizen et al. | |
| 6,349,850 B1 | 2/2002 | Cheikh | |
| 6,645,171 B1 | 11/2003 | Robinson et al. | |
| 7,959,600 B2* | 6/2011 | Chang | A61M 5/31596 604/82 |
| 8,137,307 B2* | 3/2012 | Tennican | A61M 5/31596 604/184 |
| 8,186,511 B2 | 5/2012 | Timm et al. | |
| 8,323,237 B2 | 12/2012 | Radmer et al. | |
| 8,343,130 B2* | 1/2013 | Green | A61M 5/30 604/500 |
| 8,361,035 B2 | 1/2013 | Thorley et al. | |
| 8,425,453 B2 | 4/2013 | Chang | |
| 8,522,842 B2 | 9/2013 | Sharkey et al. | |
| 8,636,689 B2* | 1/2014 | Halili, Jr. | A61J 1/2096 604/88 |
| 8,680,088 B2 | 3/2014 | Hicks, Jr. et al. | |
| 2003/0105430 A1* | 6/2003 | Lavi | A61M 5/2033 604/136 |
| 2006/0106340 A1 | 5/2006 | Goossens et al. | |
| 2006/0259020 A1 | 11/2006 | Sharratt et al. | |
| 2009/0131864 A1 | 5/2009 | Pickhard | |
| 2009/0275888 A1 | 11/2009 | Kriesel et al. | |
| 2011/0098676 A1 | 4/2011 | Chiang et al. | |
| 2012/0041366 A1 | 2/2012 | Fayyaz et al. | |
| 2012/0078172 A1 | 3/2012 | Bendek et al. | |
| 2013/0035664 A1 | 2/2013 | Mojdehbakhsh et al. | |
| 2013/0060191 A1 | 3/2013 | Thorley et al. | |
| 2013/0261046 A1 | 10/2013 | Chang et al. | |
| 2014/0066846 A1 | 3/2014 | Genosar et al. | |
| 2014/0308293 A1 | 10/2014 | Vos et al. | |
| 2015/0029816 A1 | 1/2015 | Beyer et al. | |
| 2015/0290078 A1* | 10/2015 | Li | A61J 1/1406 206/222 |

FOREIGN PATENT DOCUMENTS

| | | |
|---|---|---|
| EP | 2123316 | 11/2009 |
| WO | WO-1997020536 | 6/1997 |
| WO | WO-2001087385 | 11/2001 |
| WO | WO-2013132414 | 9/2013 |
| WO | WO-2015160563 | 10/2015 |
| WO | WO2016149457 | 9/2016 |

OTHER PUBLICATIONS

WIPO, "PCT Application No. PCT/US16/22782 International Preliminary Report on Patentability dated Sep. 28, 2017", 12 pages.

"U.S. Appl. No. 14/252,645, Final Office Action dated Nov. 17, 2017", 15 pages.

"U.S. Appl. No. 14/252,645, Non-Final Office Action dated Jun. 12, 2018", 10 pages.

"U.S. Appl. No. 14/252,645, Non-Final Office Action dated Apr. 6, 2017", 22 pages.

EPO, "EP Application No. 15779247.4, EP Search Report dated Nov. 2, 2017", NPL-135 , 8 pages.

U.S. Searching Authority, "International Application Serial No. PCT/US15/24610, Search Report and Written Opinion dated Sep. 11, 2015", 15 pages.

WIPO, "PCT Application No. PCT/US15/24610, International Preliminary Report on Patentability dated Oct. 27, 2016", 11 pages.

* cited by examiner

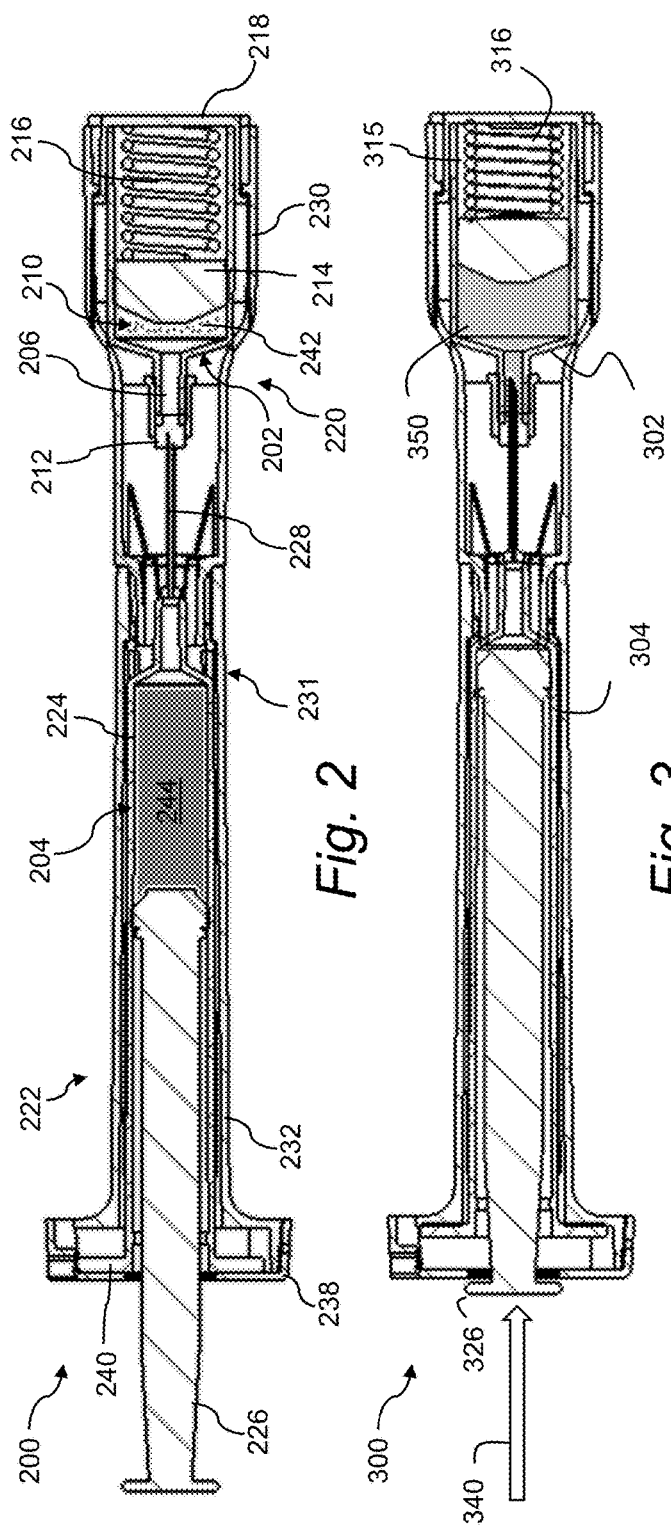

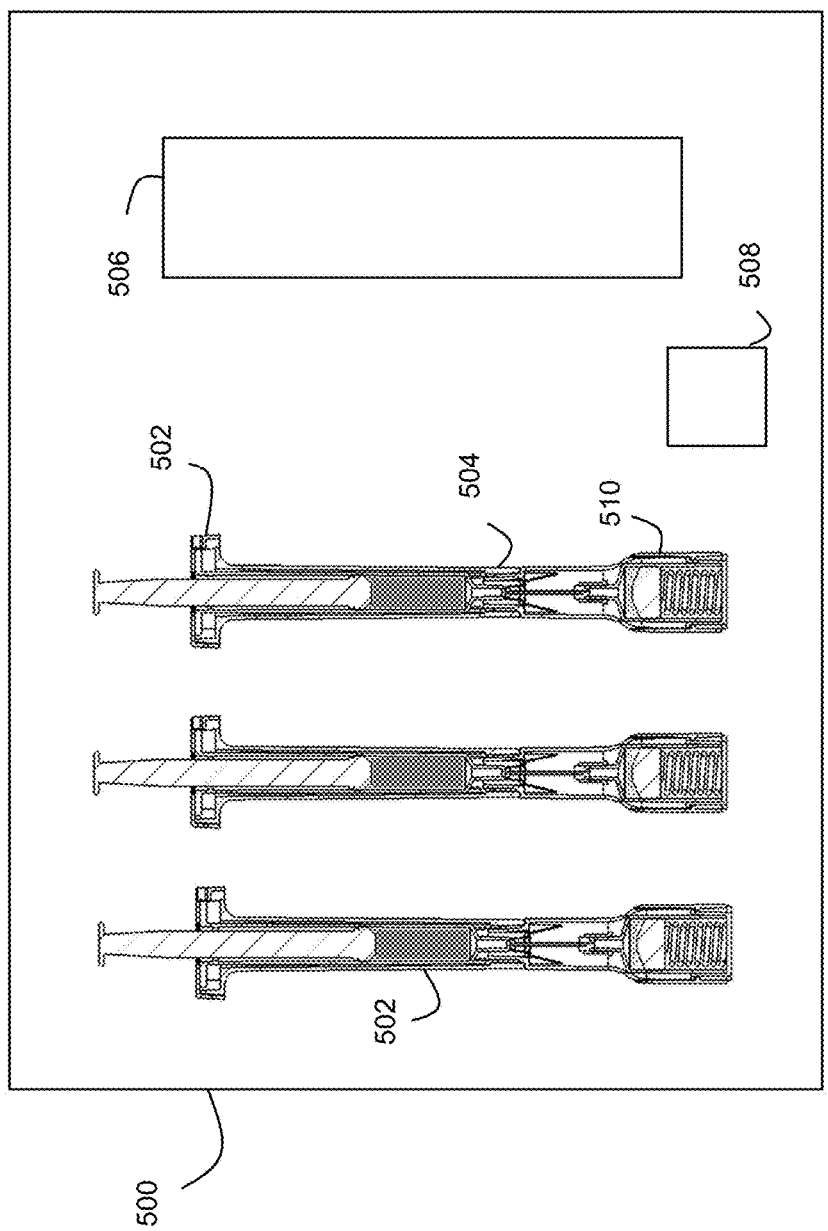

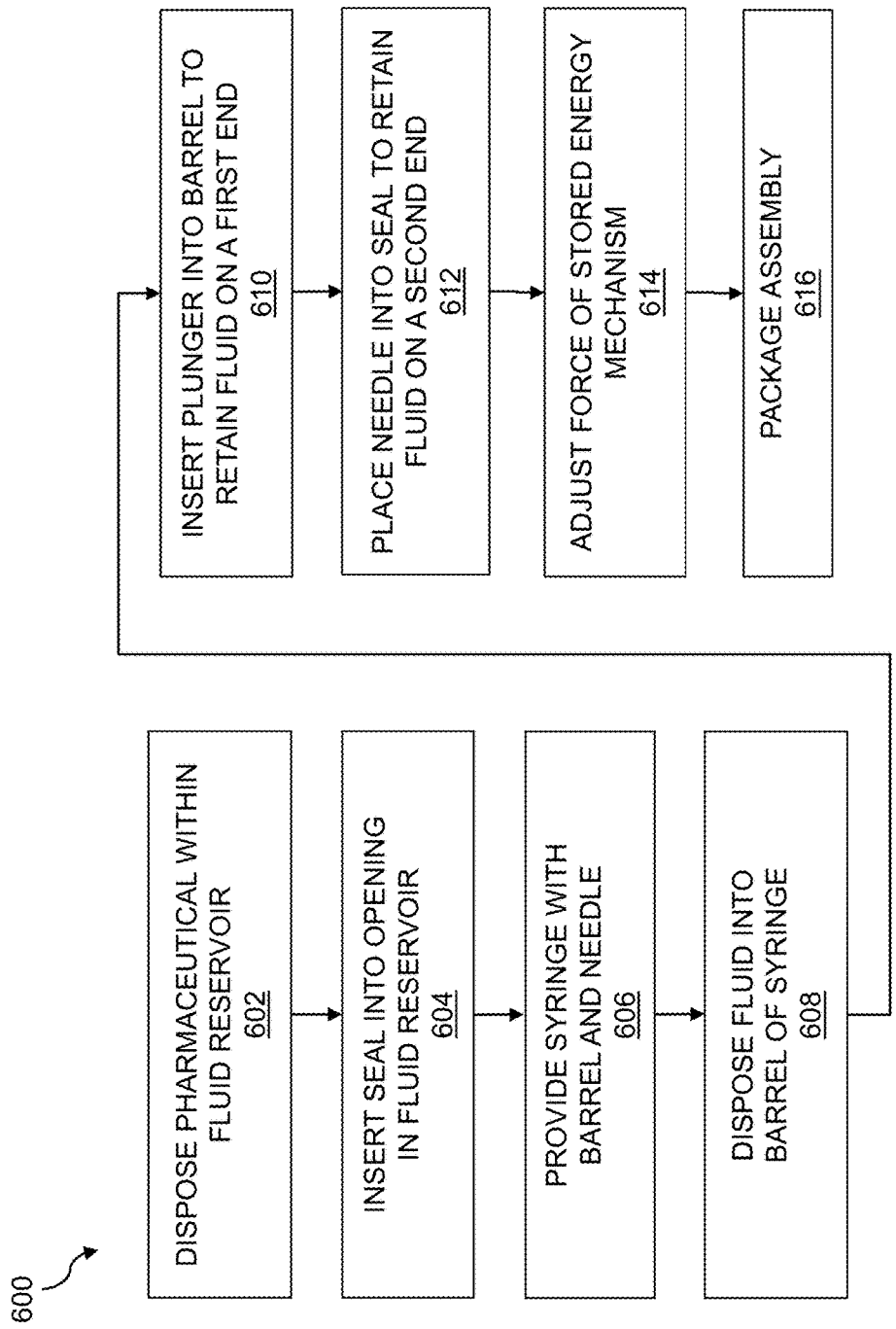

PHARMACEUTICAL RECONSTITUTION

TECHNICAL FIELD

The present disclosure generally relates to reconstitution of a pharmaceutical for injection, and more specifically to devices, systems, kits, and methods for reconstituting and injecting a pharmaceutical.

BACKGROUND

Some pharmaceuticals such as lyophilized pharmaceuticals require reconstitution immediately prior to use. This may impose particular challenges when such pharmaceuticals are intended for home use by unskilled consumers. For example, patients may be expected to manually reconstitute a lyophilized drug with bacteriostatic water (while being mindful of sterile techniques), a process requiring significant time and attention with current techniques. There is a need for improved techniques to reconstitute a pharmaceutical for injection that can reduce training time and skill required to use, decrease human error, and improve patient compliance.

SUMMARY

A device is disclosed for reconstitution and delivery of an injectable pharmaceutical. A pharmaceutical composition such as a lyophilized drug is provided in a pressurizable fluid reservoir with a pierceable seal. A diluent may be separately provided in a syringe with a needle. When the needle is driven through the seal and the plunger is actuated, fluid from the barrel of the syringe flows into the pressurizable fluid reservoir to simultaneously pressurize the reservoir and mix the diluent with the drug. Pressurized in this manner, the reservoir can then automatically and without further user intervention push the mixture back through the needle and into the barrel of the syringe, further mixing the composition and displacing the plunger to fill the barrel with the reconstituted drug. The needle and syringe can then be detached from the reservoir with the reconstituted drug contained in the barrel of the syringe and ready for injection.

BRIEF DESCRIPTION OF THE DRAWINGS

The foregoing and other objects, features, and advantages of the devices, systems, kits, and methods described herein will be apparent from the following description of particular embodiments thereof, as illustrated in the accompanying drawings. The drawings are not necessarily to scale, emphasis instead being placed upon illustrating the principles of the devices, systems, kits, and methods described herein.

FIG. 2 is a cross-sectional view of a device prior to reconstitution.

FIG. 3 is a cross-sectional view of a device in the process of reconstitution.

FIG. 4 is a cross-sectional view of a device in a ready position for use in an injection.

FIG. 5 shows a kit for reconstituting pharmaceuticals.

FIG. 6 is a flowchart of a method for packaging a device for reconstituting pharmaceuticals.

DETAILED DESCRIPTION

Figure 1:
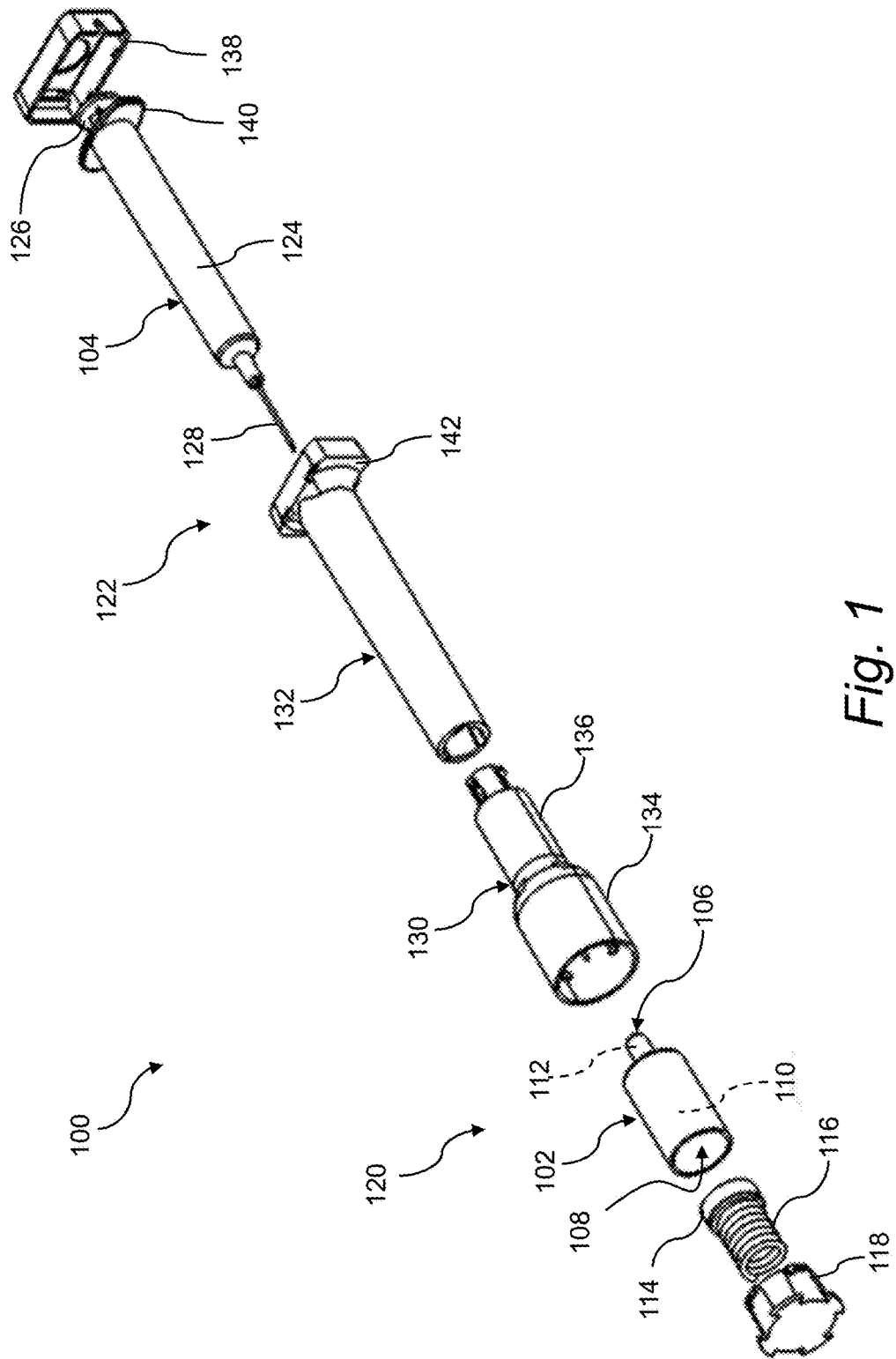
FIG. 1 is an exploded view of a device with a moving seal.

Embodiments of methods and systems for reconstitution of pharmaceuticals are described below with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the full scope of the invention to those skilled in the art.

All documents mentioned herein are hereby incorporated by reference in their entirety. References to items in the singular should be understood to include items in the plural, and vice versa, unless explicitly stated to the contrary or otherwise clear from the context. Grammatical conjunctions are intended to express any and all disjunctive and conjunctive combinations of conjoined clauses, sentences, words, and the like, unless otherwise stated or clear from the context. Thus, for example, the term "or" should generally be understood to mean "and/or" and so forth.

Recitation of ranges of values herein are not intended to be limiting, referring instead individually to any and all values falling within the range, unless otherwise indicated, and each separate value within such a range is incorporated into the specification as if it were individually recited herein. Words of approximation such as "about," "approximately," or the like, when accompanying a numerical value, are to be construed as indicating any deviation or variation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the disclosed embodiments. No language in the specification should be construed as indicating any unclaimed element as essential to the practice of the embodiments.

In the following description, it should be understood that terms such as "first," "second," "top," "bottom," "above," "below," and the like, are words of convenience only, and are not to be construed as limiting, or to imply any specific order or arrangement unless specifically stated to the contrary or otherwise clear from the context.

Any reference to "pharmaceuticals," "drugs," "injectables," "biologics," and the like, will be generally understood to include any item to be injected, e.g., through a syringe or the like. For example, the injectable may include pharmaceuticals such as proteins, peptides, biologics, vaccines, enzymes, microorganisms, monoclonal antibodies, parenterals, pharmaceuticals, blood fractions, oglionucleotides, blood plasma, diagnostics, nutraceuticals, cosmeceuticals, biomaterials, and so on. The pharmaceutical may be in powder form. The pharmaceutical may require reconstitution, rehydration, mixing, or the like, to place the pharmaceutical into an injectable form. The pharmaceutical may include a lyophilized pharmaceutical that has undergone a freeze-drying process or the like. For example, the lyophilized pharmaceutical may include injectable human chorionic gonadotropin (HCG), e.g., to treat hypogonadism, or an immunoresponsive biologic such as a vaccination.

The systems and methods described herein may be usefully employed in any context where an injectable composition might be prepared for storage or transportation in a lyophilized, concentrated, dehydrated, or other reconstitutable form. The devices, systems, kits, and methods described herein may, for example be integrated into or use techniques described in U.S. patent applicaiton Ser. No.

14/252,645, filed on Apr. 14, 2014, incorporated by reference herein in its entirety, with variations and modifications as described below.

In a general embodiment, a device described herein includes a pressurizable fluid reservoir on one hand and a syringe on the other. The pressurizable fluid reservoir has a dry pharmaceutical composition contained within the reservoir by a moving seal on one end and a pierceable seal on the other end. The syringe can be preloaded with a diluent, and then a needle of the syringe can be inserted into the pierceable seal of the reservoir. In this configuration, a plunger of the syringe can be depressed to first drive the needle through the pierceable seal and then push the diluent from the syringe into the pressurizable fluid reservoir where the diluent displaces the moving seal and pressurizes the reservoir. The pressure in the reservoir can then be used to return the mixture of pharmaceutical and diluent back into the syringe, automatically displacing the plunger into a ready position for injection. The syringe can then be simply withdrawn or detached from the fluid reservoir and used as indicated.

FIG. 1 is an exploded view of a device with a moving seal. The device 100 may generally be a device for reconstituting and injecting a pharmaceutical. The device 100 may provide a complete "one-and-done" system for an injectable such as a reconstituted pharmaceutical. The device 100 may be partially disposable, completely disposable, or non-disposable (i.e., reusable). The device 100 may be a single-dose or multi-dose device. The device 100 may be adapted for use with a range of injectables such as any of the injectables described herein.

In general, the device 100 may include a fluid reservoir 102 and a syringe 104, which may cooperate with one another using various subcomponents to reconstitute a pharmaceutical for injection. The fluid reservoir 102 and syringe 104 (and associated subcomponents) may form the complete device 100 or they may be utilized independently as separate devices.

The fluid reservoir 102 may include a first opening 106 on a top portion thereof, and a second opening 108 on a bottom portion thereof. The fluid reservoir 102 may contain a dry pharmaceutical composition disposed within a chamber 110 of the fluid reservoir 102 between the first opening 106 and the second opening 108. For example, the fluid reservoir 102 may contain a lyophilized pharmaceutical such as human chorionic gonadotropin (HCG) or an immunoresponsive biologic. The fluid reservoir 102 may be made from any material known in the art, including, without limitation, glass, plastic, metal, rubber, and so on. For example, the fluid reservoir 102 may be made from neoprene to take advantage of its inherent sealing and waterproof characteristics, or the fluid reservoir 102 may be made from the same material as a standard syringe. In one aspect, the fluid reservoir 102 may include a barrel of a standard syringe or device of similar construction that is adapted for the purposes of the device 100. In an aspect, the fluid reservoir 102 has a diameter of about 0.44 inches capable of holding about 1.5 cc of fluid of the same height (e.g., water). In one aspect, a 10 cc syringe may be used as the fluid reservoir 102, which has an inner diameter of about 0.65 inches. In one aspect, the fluid reservoir 102 may have a leak-free fluid storage capacity. The fluid reservoir 102 may include a single fixed dose of a pharmaceutical so that, once reconstituted, the fluid reservoir 102 may be used with the syringe 104 or the like to manually inject the reconstituted pharmaceutical into a patient. Alternatively, the fluid reservoir 102 may have a capacity to contain multiple doses, which may further require refrigeration after an initial reconstitution of the pharmaceutical.

The fluid reservoir 102 may be pressurizable using a stored energy mechanism 116 that stores energy as fluid is delivered into the fluid reservoir 102. This pressurized fluid in the interior can then be automatically returned to its source or otherwise evacuated from the reservoir under pressure provided by the stored energy mechanism 116. In one aspect, the stored energy mechanism 116 for the fluid reservoir 102 may be preloaded with a spring or the like before a fluid is added to the chamber in order to facilitate a more complete evacuation of the fluid reservoir 102 after fluid is added. In another aspect, the fluid reservoir 102 may only be pressurized after a fluid is added to the chamber 110, e.g., by injecting a fluid into the chamber 110. In this latter embodiment, the stored energy mechanism 116 may be configured to receive additional energy, e.g., by compressing a spring or the like, after the fluid is added to the fluid reservoir 102 in order to facilitate a more complete evacuation. The fluid reservoir 102 may thus include a variety of stored energy elements to facilitate pressurization, such as a moving seal and a spring or the like on an end of the fluid reservoir 102.

The fluid reservoir 102 may include a first seal 112 forming a pierceable cover for the first opening 106 where a syringe needle can be inserted in a sealed engagement with the fluid reservoir 102 and then removed while preserving a liquid seal maintained by the first seal 112. Pressurization may be supported by a second seal 114 that is movable within the fluid reservoir 102 and forms a seal for the second opening 108, along with the stored energy mechanism 116 that cooperates with the second seal 114 to store energy in the form of fluid pressurization and return energy by driving the second seal 114 to expel fluid from the fluid reservoir 102 through the first opening 106.

The first seal 112 may form a pierceable, self-sealing cover for the first opening 106 of the fluid reservoir 102. The first seal 112 may be integral with the fluid reservoir 102 or otherwise attached to the first opening 106, and may seal the first opening 106 at or above a pressure within the fluid reservoir 102. This interior pressure may, for example, be a pressure created by a force applied to contents of the fluid reservoir 102 by the stored energy mechanism 116. It will be understood that the pressure may vary during a use of the device 100, for example when fluid is injected into and then evacuated from the fluid reservoir 102. In general, the first seal 112 may be configured to provide fluid seal up to a maximum expected pressure, or some predetermined amount beyond that maximum expected pressure in order to provide a suitable safety margin. The first seal 112 may be formed of any material suitable for separating an interior of the fluid reservoir 102 from environmental conditions. For example, the first seal 112 may be formed from a low-durometer rubber, which may include, without limitation, one or more of neoprene and polyisoprene. In an implementation, the first seal 112 may also or instead include a membrane that acts as a barrier for the chamber 110.

The first seal 112 may use a Luer lock system or the like to achieve a complete seal of the fluid reservoir 102. In an aspect, a rubber seal may be used as the first seal 112 to concurrently seal and separate the contents of the syringe (e.g., a diluent) and the fluid reservoir (e.g., a dry pharmaceutical). The rubber seal may be formed of about a 0.17-inch thick neoprene piece inserted into a female Luer lock fitting of a syringe having its needle portion removed. In one aspect, a ventilated female Luer lock cap may be used (e.g., a female Luer lock fitting without the needle). This may be any commercially available female Luer lock fitting or any other suitable biocompatible junction or connector.

The first seal 112 may be retained within the fluid reservoir 102 using an interference fit, through structural supports, or by any means known in the art sufficiently for retaining the first seal 112 during handling and use. For example, the retaining means should be sufficiently strong to retain the first seal 112 in the first opening 106 of the fluid reservoir 102 when the chamber 110 is pressurized as contemplated herein, as well as when a downward force is applied, e.g., by a user pushing a needle of a syringe and piercing the first seal 112 to couple the interior of the syringe to the interior of the fluid reservoir 102. In one aspect, an interference fit is provided through the use of a first seal 112 having a diameter that is at least 0.004 inches larger than the 0.14-inch inner diameter of the female fitting, or sufficiently large to provide a robust fluid-tight seal under pressure without fracturing the fluid reservoir 102.

The second seal 114 may be a moving seal within the fluid reservoir 102. The second seal 114 may be located within the fluid reservoir 102 where it forms a barrier between the chamber 110 of the fluid reservoir 102 and a stored energy mechanism 116. The second seal 114 may form a fluid seal within the fluid reservoir 102 in the same manner as the plunger of a syringe using any suitable shape and material suitable for sealing a fluid and/or a pharmaceutical composition within the fluid reservoir 102 under conditions (e.g., pressures) contemplated herein. Thus, in one aspect, the second seal 114 may include a plunger seal or the like (i.e., a plunger seal of a typical syringe) that is sized to slide within an interior of the fluid reservoir 102 while maintaining a fluid seal to retain a fluid and/or a pharmaceutical composition within the interior of the fluid reservoir 102. The first seal 112 and the second seal 114 can cooperate to isolate the dry pharmaceutical composition included in the interior of the fluid reservoir 102 from environmental conditions prior to reconstitution of the pharmaceutical composition for injection or other use. The first seal 112 and the second seal 114 may also isolate a mixture of the dry pharmaceutical composition and a diluent from environmental conditions during reconstitution but prior to delivery of the mixture into a syringe for injection.

The second seal 114 may be connected to the stored energy mechanism 116 so that the stored energy mechanism 116, e.g., a coil spring or the like, is compressed when the chamber 110 of the fluid reservoir 102 is filled with fluid during a reconstitution stage (as discussed in more detail below). The stored energy mechanism 116 may return stored energy by pushing the second seal 114 toward the first seal 112 within the fluid reservoir 102 and displacing contents of the fluid reservoir 102 into the syringe 104 to place the device 100 in an injection-ready stage. The second seal 114 may also or instead include a membrane such as an elastic membrane or an inelastic membrane within a pressurizable chamber 315. This membrane may, e.g., separate an interior of the fluid reservoir 102 from a pressurizing chamber that includes a pressurized gas (e.g., air) or the like. In another aspect, the membrane may be an elastic membrane that elastically stores energy as it expands.

As discussed above, the device 100 may further include a stored energy mechanism 116 configured to pressurize an interior of the fluid reservoir 102, e.g., by applying a force to the second seal 114 (i.e., the moving seal) with a mechanical spring such as a coil spring or the like. For example, the stored energy mechanism 116 may include a spring biased between the second seal 114 and a first cap 118 thereby applying a force to the second seal 114 and preloading the stored energy mechanism 116. In this manner, a greater force may be provided to evacuate fluid inside the fluid reservoir 102, such as fluid forced into the fluid reservoir 102 through the first opening 106 from the barrel of a syringe as contemplated herein. The stored energy mechanism 116 may also or instead include a compressible fluid pressurized to apply a force to the second seal 114.

In one aspect, the stored energy mechanism 116 may include a pre-loaded spring with a spring constant of about 1.73 N/mm compressed to provide enough force to push about 1.5 cc of water through a 22G needle (or the like) into a 3 cc syringe (or the like) in about 4.4 seconds. For example, a spring from McMaster-Carr (Product #9657K312) may be used. In one aspect, the spring may include a coil spring having an outer diameter smaller than the inner diameter of the fluid reservoir 102. The stored energy mechanism 116 may also or instead include a pressurized gas (e.g., air) within the fluid reservoir 102, or in a pressure chamber disposed adjacent to the second seal 114 or otherwise separated from the fluid reservoir 102 by a membrane or the like.

The first cap 118 may be placed on a first end 120 of the device 100 to seal or otherwise secure the fluid reservoir 102. The first cap 118 may be permanently or releasably coupled to the stored energy mechanism 116 (e.g., the spring shown in FIG. 1), or otherwise engaged with and/or forming a part of the stored energy mechanism 116. The first cap 118 may be removably and replaceably coupled to the fluid reservoir 102. The first cap 118 may also be coupled to the second seal 114, so that removing the first cap 118 also removes or releases the second seal 114 thereby providing access to the chamber 110 within the fluid reservoir 102. Alternatively, the first cap 118 may be permanently attached to the fluid reservoir 102, e.g., using an adhesive, an ultrasonic weld, or any other suitable bonding technique known in the art. In this manner, placing the first cap 118 on the distal end 120 of the device 100 may apply a force to the stored energy mechanism 116 (e.g., by compressing a spring) thereby pressurizing the interior of the fluid reservoir 102. The first cap 118 may be configured to engage the stored energy mechanism 116 with the second seal 114 when coupled to the fluid reservoir 102. The first cap 118 may include a screw thread or bayonet feature that engages with a corresponding screw thread on a housing, an alignment fixture (described below), or the fluid reservoir 102 in order to provide a stable and consistent interaction between the components of the device 100. It will be understood that while the first cap 118 and second seal 114 are periodically described herein as separate from the stored energy mechanism 116, these parts and any other components cooperating therewith may also form a part of a stored energy mechanism 116. More generally, any component or combination of components that can cooperate to receive, store and release energy as contemplated herein, either inclusive or exclusive of other, cooperating components, may be considered to form the stored energy mechanism 116 as that term is used herein, unless a different meaning is expressly provided or otherwise clear from the context.

Any reference herein to coupling, connecting, engaging, fitting, or the like, for example, through interference fits, snap-fits, screw fits/threads, may also or instead include any of the other means for connection discussed herein or otherwise known in the art. For example, these connections may also or instead include, without limitation, clamps, clips, friction fits, hooks, latches, pins, sliders, and so forth. In other words, a skilled artisan will understand that the components of the devices, systems, kits, and methods described herein may be connected and assembled through numerous means known in the art.

As discussed above, the device 100 may also include a syringe 104 that cooperates with the fluid reservoir 102 and the other components described herein to reconstitute a pharmaceutical. The syringe 104 may be disposed on the second end 122 of the device 100. The syringe 104 may include a barrel 124, a plunger 126, and a needle 128. The syringe 104 may be used for injecting a fluid into the fluid reservoir 102 and/or for injecting a reconstituted pharmaceutical into a user or patient. The syringe 104 may include any suitable syringe such as a 3 milliliter VitaNeedle (Part #SY707) or BD Luer-Lok (Part #309657) syringe, or any other disposable over-the-counter syringe or the like. A skilled artisan will recognize that other sizes and designs of syringes may be used in the devices, systems, kits, and methods described herein. Where a non-standard syringe is used, the syringe 104 may optionally operate with similar interaction forces to reproduce the feel of a standard over-the-counter-syringe. In one aspect, the syringe 104 may include an automatic injector.

The syringe 104 may include an amount of fluid to reconstitute a single fixed dose of a pharmaceutical. After this fluid is injected from the syringe 104 into the fluid reservoir 102, the syringe 104 may also receive the resulting, reconstituted pharmaceutical (delivered by the stored energy mechanism 116) so that the syringe 104 can be used to inject the reconstituted pharmaceutical into a patient without further processing steps or handling. To this end, the barrel 124 may be sized to contain an amount of fluid selected to reconstitute a single dose of the pharmaceutical in the chamber 110 of the fluid reservoir 102 and to receive the single dose of the reconstituted pharmaceutical for injection. The barrel 124 may also or instead have an interior volume sized for multiple doses, which may be reconstituted collectively and then used within some predetermined shelf life. In a multi-dose configuration, the syringe 104 may be refrigerated or otherwise stored to preserve or extend the life of the reconstituted pharmaceutical as appropriate. The fluid in the barrel 124 of the syringe 104 may include any suitable liquid diluent such as a bacteriostatic solvent (e.g., bacteriostatic water).

While engaged with the fluid reservoir 102, the plunger 126 of the syringe 104 may seal one end of the syringe 104, and the first seal 112 may seal the other end of the syringe 104, e.g., through the partial insertion of the needle 128 into the first seal 112. This configuration may securely contain the fluid (e.g., diluent) in the barrel 124 of the syringe 104 where it can remain isolated from environmental conditions until ready for use.

The device 100 may include one or more alignment fixtures, e.g. a first alignment fixture 130 and a second alignment fixture 132 to stabilize and provide for cooperation of the fluid reservoir 102 and the syringe 104, such as by orienting the syringe 104 in an appropriate orientation and position for use with the fluid reservoir 102.

The first alignment fixture 130 may be coupled to the fluid reservoir 102. For example, the first alignment fixture 130 may engage the fluid reservoir 102 and be shaped and sized such that the first alignment fixture 130 retains the fluid reservoir 102 within a first barrel 134. The first cap 118 may engage with the first alignment fixture 130 and/or the fluid reservoir 102 using threads, and interference fit, or any other permanent or reusable attachment mechanism in order to retain the fluid reservoir 102 within the first barrel 134 and to retain the second seal 114 within the fluid reservoir 102. For example, a clearance fit may be employed for an easy insertion of the fluid reservoir 102 into the first barrel 134, or the parts may be coupled with a threaded connection or any other suitable coupling. Where a standard 10 cc syringe barrel is used for the fluid reservoir 102, the inner diameter of the first barrel 134 may be about 0.66 inches to provide about 0.01 inches of clearances from the fluid reservoir 102. The first alignment fixture 130 may further include a second barrel 136 that is shaped and sized to assist in retaining the fluid reservoir 102 within the first barrel 134 and to couple the first alignment fixture 130 with the second alignment fixture 132.

The second alignment fixture 132 may be shaped and sized to stabilize the syringe 104 and retain the syringe 104 in a desired position and orientation relative to the fluid reservoir 102. Specifically, the second alignment fixture 132 may be configured to engage with a second cap 138 to house the syringe 104 within the second alignment fixture 132 such that the syringe 104 is aligned for engagement with the fluid reservoir 102. The second alignment fixture 132 may serve as a container for the syringe 104 as well as a handle for a user during reconstitution, injection, and safe disposal. A clearance fit may be employed between the syringe 104 and the second alignment fixture 132 permitting the syringe 104 to travel axially within the interior of the second alignment fixture 132. To achieve this clearance fit, a hole in the approximate center of the second alignment fixture 132 may have a diameter that is larger (e.g., about 0.01 inches larger) than an outer diameter of the syringe 104. In this manner, there may be a loose interference fit between the outer diameter of the body of the syringe 104 and the inner diameter of the second alignment fixture 132 so that the syringe 104 and the second alignment fixture 132 can be slidably coaxially engaged with one another. One or more features may be provided to mechanically key the second alignment fixture 132 to the syringe and retain the syringe 104 in a desired position and orientation. The second alignment fixture 132 may enforce a desired position of the needle 128 relative to the fluid reservoir 102. The second alignment fixture 132 may also or instead engage the flange 140 of the syringe 104 such that the plunger 126 is exposed out of the second end 122 of the device 100.

The second alignment fixture 132 may include a support 142 or the like to engage and guide the syringe flange 140, e.g., the thumb tabs provided on a conventional syringe for handling and injection. In an aspect, the support 142 facilitates use of the device 100 by aligning the syringe 104 axially to the opening 106 in the fluid reservoir 102, and positioning the syringe 104 at a suitable distance for further cooperation as contemplated herein. For example, the support may provide stops for different axial positions of the syringe 104 during use. In a first axial position, the needle 128 of the syringe 104 may be not yet in contact with the first seal 112, or contacting the first seal (e.g., embedded into the material of the first seal 112), but not yet penetrating through the first seal 112. In a second axial position, the needle 128 of the syringe 104 may pass through the first seal 112 into an interior of the fluid reservoir 102.

With a first and second axial stop as described above, the syringe 104 cannot be discharged into the chamber 110 of the fluid reservoir 102 while in the first axial position, which may help to prevent premature mixing of a diluent and dry pharmaceutical. In the second axial position, the needle 128 may pass through the first seal 112 into the chamber 110, but preferably not so far that the needle 128 contacts the second seal 114 or otherwise damages the interior of the fluid reservoir 102. To this end, the support may be shaped and sized for a specific syringe displacement between the first axial position and the second axial position during use, e.g., such that the syringe 104 travels from the first axial position to the second axial position when a user applies a force to the top of the syringe 104 or otherwise activates the device 100. For example, in an aspect, when a user presses the plunger 126 or flange 140 to the point where the flange 140 of the syringe 104 meets a surface of the support 142, the aperture of the needle 128 may travel a sufficient distance to pass through the first seal 112 into the fluid reservoir 102 and couple the syringe 104 in fluid communication with the reservoir 102 to initiate the reconstitution. If 22G, ¾ inch needles are used for the device 100, the length of the needle aperture may be about 0.115 inches. To ensure that the aperture passes fully through the first seal 112 and into the fluid reservoir 102 (which may include about a 0.17 inch-thick rubber seal), a safety factor of two may be used for the aperture length, which consequently sets the height of the support 142 to about 0.23 inches. The support 142 may also engage the flange 140 of the syringe 104 so that force can be applied to the plunger 126 to drive fluid into the fluid reservoir 102.

The second alignment fixture 132 may also or instead include any number of safeties, stops, locks, or the like for establishing or maintaining one or more axial positions of the syringe 104, such as the first and second axial positions described above. In one aspect, the second cap 138 may provide a safety or the like configured to controllably secure and release the syringe 104 at a desired axial position. For example, the second cap 138 may slide perpendicular to the axis of the syringe, and may include one or more flanges or the like that engage the flange 140 of the syringe 104 in one position to prevent axial displacement toward the fluid reservoir 102, and release the flange 140 of the syringe 104 in a second position to permit axial displacement toward the fluid reservoir 102.

The first alignment fixture 130 may engage with the second alignment fixture 132 using any of the connection means described herein or known in the art, including without limitation, screw threads, interference fit, and so forth. When engaged, the first alignment fixture 130 and the second alignment fixture 132 may be locked into place relative to one another, e.g., through a self-locking interaction. By placing the first cap 118 on the first alignment fixture 130 the stored energy mechanism 116 may be compressed to preload the stored energy mechanism, and then by placing the second cap 138 on the second alignment fixture 132 with the syringe 104 contained therein the entire system may be isolated from environmental conditions, completing the assembly of the device 100. One or more of the first alignment fixture 130 and the second alignment fixture 132 can be disconnected and shed upon activation to leave an injection-ready syringe 104.

The alignment fixtures 130, 132 may be coupled to the fluid reservoir 102, and shaped and sized to retain a needle 128 and a syringe 104 of predetermined dimensions in a position and orientation with the needle 128 partially breaching the first seal 112 to form a barrier between the interior of the fluid reservoir 102 and an interior of the syringe 104. This configuration advantageously maintains concurrent and physically separated reservoirs for the dry pharmaceutical composition (in the fluid reservoir 102) and a fluid (in the interior of the syringe 104). The alignment fixtures may enforce other positions and orientations, such as with the needle aligned with but not yet touching the first seal 112, or with the needle 128 fully passing through the first seal 112 and extending into the interior of the fluid reservoir 102 so that the fluid reservoir is coupled in fluid communication with the interior of the syringe 104. In an embodiment where the syringe 104 is positioned with the needle 128 in the fluid reservoir 102, additional membranes or packaging may be employed to isolate contents of the diluent and dry pharmaceutical until mixing is initiated by a user.

The second cap 138 may generally include a cap for the second end 122 of the device 100. The second cap 138 may retain the syringe 104 within the alignment fixture 132 and provide a barrier to prevent the user from accidentally pulling the syringe 104 out of the alignment fixture 132 or otherwise mishandling the device 100. In an aspect, the second cap 138 may include a mechanism to engage and release flanges of the syringe 104 in order to controllably and releasably retain the syringe 104 in a predetermined axial position relative to the fluid reservoir 102.

FIG. 2 is a cross-sectional view of a device prior to reconstitution. Specifically, the device 200 may be configured just prior to reconstitution, but after alignment features (e.g., the alignment fixture 231 described herein) have been assembled or engaged with all components therein, thus forming a reconstitution-ready device. The device 200 may include a fluid reservoir 202 and a syringe 204. As generally described above, the fluid reservoir 202 may include a first opening 206, a chamber 210, a first seal 212, a second seal 214, and a stored energy mechanism 216. The syringe 204 may include a barrel 224, a plunger 226, a needle 228, and a flange 240. The device 200 may further include a first cap 218 on a first end 220, a second cap 238 on a second end 222, and an alignment fixture 231.

In a pre-use state, the fluid reservoir 202 may contain a pharmaceutical 242, such as a dry pharmaceutical composition that requires reconstitution prior to injection into a patient. To begin assembly of the first end 220 of the device 200, the first opening 206 of the fluid reservoir 202 may be sealed by the first seal 212, which forms a pierceable cover for the first opening 206. The pharmaceutical 242 may then be disposed within the chamber 210 of the fluid reservoir 202 through an opposing end that is subsequently sealed by the second seal 214, which includes a moving, air-tight seal. Thus, the second seal 214 may seal the second opening (shown covered by the first cap 218 in FIG. 2) of the fluid reservoir 202.

In one aspect, after placing the pharmaceutical 242 in the fluid reservoir 202 and inserting the second seal 214, the first seal 212 is removed and the second seal 214 is axially displaced until air is pushed out of the chamber 210 of the fluid reservoir 202. Then, the fluid reservoir 202 is re-capped with the first seal 212. In another aspect, the second seal 214 is axially displaced within the fluid reservoir 202 until a remaining space in the chamber 210 has substantially the same volume as the pharmaceutical 242. The pharmaceutical 242 may then be disposed within the chamber 210 of the fluid reservoir 202 through the first opening 206, which is subsequently sealed by the first seal 212.

The second seal 214 may be engaged with the stored energy mechanism 216, e.g., a coil spring, which is disposed between the second seal 214 and the first cap 218 as shown in FIG. 2. The first cap 218 may be threaded onto or otherwise attached to at least one of the fluid reservoir 202 and the alignment fixture 231 to retain the stored energy mechanism 216 between the second seal 214 and the first cap 218. In the pre-reconstitution state, the stored energy mechanism 216 may be in a relaxed state (e.g., the coil spring is elongated or otherwise not fully compressed). In this relaxed state, the stored energy mechanism 216 is applying a lesser amount of force onto the second seal 214 than when the stored energy mechanism 216 is in a pressurizing state (e.g., the coil spring is compressed). In another aspect, the stored energy mechanism 216 may be in a semi-pressurizing state (e.g., the coil spring is partially compressed) when the device 100 is in the pre-reconstitution state. This latter configuration advantageously provides greater return force when driving a mixed composition within the fluid reservoir 202 back into the syringe 204.

In one aspect, after placing the pharmaceutical 242 in the fluid reservoir 202 and inserting the second seal 214, the first seal 212 is removed and the second seal 214 is axially displaced until air is pushed out of the chamber 210 of the fluid reservoir 202. Then, the fluid reservoir 202 is re-capped with the first seal 212.

However assembled, the fluid reservoir 202 may be placed inside of an alignment fixture 231. The alignment fixture 231 may be shaped and sized to align and configure the fluid reservoir 202 and the syringe 204 for operation of the device 200 as contemplated herein. The alignment fixture 231 may include the syringe 204 therein, or the syringe 204 may be subsequently added to the alignment fixture 231. In an aspect, the alignment fixture 231 includes a first alignment fixture 230 for retaining the fluid reservoir 202, and a second alignment fixture 232 for retaining the syringe 204, where the first and second alignment fixtures combine to form the alignment fixture 231 of the device 200.

Once the fluid reservoir 202 is in place, the syringe 204 containing an appropriate amount of a fluid 244 (e.g., a liquid diluent) for reconstituting the pharmaceutical 242 may be placed within the second end 222 of the device 200. In an aspect, the syringe 204 is placed within the second alignment fixture 232 and the second cap 238 is fitted to the second end 222 of the device 200 by any means known in the art. The flange 240 of the syringe 204 may be retained by a stop or the like on the second cap 238, and engagement of the second cap 238 and the syringe 204 can occur before engagement with the second alignment fixture 232. The stop or the like on the second cap 238 may prevent inadvertent axial movement of the syringe 204 within the device 200. More generally, any technique for securely positioning the syringe 204 in a predetermined axial position and orientation relative to the fluid reservoir 202 may be employed, including any of a variety of mechanisms to removably and replaceably secure the syringe 204 in the device 200 where the plunger 226 is accessible.

Once the syringe 204 is in place, the first alignment fixture 230 may be coupled to the second alignment fixture 232. The coupling of the first alignment fixture 230 and the second alignment fixture 232 may be through any means known in the art, e.g., they may be screwed together, snapped together (e.g., with a flanged rim), coupled with an interference fit, and so forth. Once the first alignment fixture 230 and the second alignment fixture 232 are coupled, the device 200 may be in a pre-reconstitution state.

In the pre-reconstitution state, the alignment fixture 231 may retain the needle 228 of the syringe 204 in a position and orientation with the needle 228 partially breaching the first seal 212 to form a barrier between the chamber 210 of the fluid reservoir 202 and an interior of the syringe 204 to concurrently and separately retain the pharmaceutical 242 in the fluid reservoir 204 and the fluid 244 in the interior of the syringe 204.

In a manufacturing process, the assembly described herein may be aided by automated filling equipment, e.g., in order to ensure accurate filling of the pharmaceutical/fluid, the purging of all air, the sealing of the pharmaceutical/fluid from environmental conditions, and so forth. One skilled in the art will recognize that other assembly methods may also or instead be used and are intended to fall within the scope of this disclosure.

FIG. 3 is a cross-sectional view of a device in the process of reconstitution (or after reconstitution but before a reconstituted pharmaceutical is loaded into a syringe or the like for injection). Specifically, FIG. 3 shows a device 300 after a needle has pierced the first seal enabling communication of the interior of a syringe 304 and a fluid reservoir 302. The device 300 may, for example, be any of the devices described herein. In use, the plunger 326 may be depressed into the barrel of the syringe 304 as generally illustrated by an arrow 340, thus driving the diluent from the barrel, through the needle, and into the fluid reservoir 302 where the fluid can mix with the pharmaceutical for forming a mixture 350. As a result of this action, the stored energy mechanism 316 may receive the energy provided by the depressing plunger, and store this energy for subsequent use. In an aspect, a user may be required to maintain the position shown in FIG. 3 where the plunger 326 is fully depressed for a predetermined amount of time to enable adequate formation of the mixture 350. Alternatively, a system automating this process, or similar, can be used.

FIG. 4 is a cross-sectional view of a device in a ready position for use in an injection. As described above, with the interior of the syringe 404 coupled in fluid communication with the fluid reservoir 402, the stored energy mechanism 416 may release energy by driving the contents of the fluid reservoir 402 back into the syringe 404 thus further mixing the contents 450, displacing the plunger 426 as illustrated by an arrow 440, and placing the syringe 404 in a ready state for injection. At this point, the syringe 404 may be removed or separated from the alignment fixture(s) of the device 400 and used as indicated by a patient.

FIG. 5 shows a kit for reconstituting pharmaceuticals. In general, the kit 500 may include one or more devices 502, each including a syringe, a needle fitted to the syringe, and a plunger fitted to the syringe, all as described above. In addition, each device 502 may include a vessel for a dry pharmaceutical, such as any of the fluid reservoirs described above with an opening, a seal forming a pierceable, self-sealing cover for the opening, a moving seal within the reservoir and a stored energy mechanism configured to pressurize a fluid within the reservoir by applying a force to the moving seal, which may include any of the components described above.

Each device 502 may further include alignment fixtures 504 and other components as generally contemplated herein for single-use or multi-use reconstitution and injection of pharmaceuticals or the like. In one aspect, a multi-use kit may be configured with a single alignment fixture 504 and multiple syringes. In another aspect, a multi-use kit may include a separate, disposable alignment fixture 504 for each one of a plurality of syringes. As described above, each alignment fixture 504 may removably and replaceably secure a syringe in a location where the needle, when attached to the syringe, pierces the seal of the reservoir to couple a barrel of the syringe in fluid communication with the reservoir. The alignment fixture 504 may usefully integrate a sharps container to enclose the needle after use, thus facilitating safe disposal of the used device. The alignment fixture may also or instead include a separable sleeve adapted to separate from the alignment fixture and cover the needle after use, such as the second alignment fixture for the syringe described above, or any other suitable sleeve suitably shaped to cover the exposed needle.

As described above, the pharmaceutical in the device may include a lyophilized pharmaceutical and the kit may include a reconstituting fluid within the syringe such as water. The kit may be a single use kit, or the kit may be a multi-use kit including a plurality of syringes and a corresponding plurality of vessels each with a predetermined dosage of a pharmaceutical selected for a particular patient. In one aspect, the kit 500 may additionally include a sharps container 506 for disposal of the needle. In another aspect, the kit 500 may include an antiseptic 508 for use in cleaning an injection site. The antiseptic may, for example, include one or more of an anti-bacterial, an isopropyl alcohol, or a hydrogen peroxide. The antiseptic may be packaged as an alcohol swab or other item suitable for use in cleaning an injection site. The antiseptic 508 may be provided as a separate item within the kit 500, or the antiseptic may be usefully integrated into an exterior surface of the vessel 510 or other component of one of the devices 502 for convenient access by a user.

FIG. 6 is a flowchart of a method for packaging a device for reconstituting pharmaceuticals.

As shown in step 602, the method 600 may begin with disposing a pharmaceutical within an interior of a fluid reservoir. The pharmaceutical and the fluid reservoir may be as generally described herein. As noted above, the stored energy mechanism may be capable of pressurizing the fluid reservoir, e.g., by incorporating a coil spring or the like that compresses as fluid is added to the fluid reservoir. In one aspect, the pharmaceutical may include a lyophilized pharmaceutical, and disposing the pharmaceutical within the fluid reservoir may include lyophilizing the pharmaceutical directly into the fluid reservoir.

As shown in step 604, the method 600 may include inserting a seal into an opening in the fluid reservoir, such as any of the pierceable, self-sealing seals described herein.

As shown in step 606, the method may include providing a syringe. The syringe may in general be any of the syringes or similar devices described herein, and may include a barrel and needle.

As shown in step 608, the method 600 may include disposing a fluid into the barrel of the syringe. This may include manual or automated filling, and may be performed in a sterile environment in order to maintain conditions suitable for subsequent injection.

It will be understood that, while the final assembly may be shipped preloaded with fluid in the syringe, syringes may also or instead be shipped with a separate supply of fluid. Thus step 608 may alternatively or additionally include providing an amount of fluid for reconstituting the pharmaceutical and packaging the amount of fluid in the package. In this embodiment, the fluid may be disposed inside the barrel as contemplated above, or the amount of fluid may be provided separately in a sterile fluid container such as an injection fluid container with a pierceable seal from which the syringe can be filled by an end user.

As shown in step 610, the method 600 may include inserting a plunger into the barrel to retain the fluid within the barrel on a first end.

As shown in step 612, the method 600 may include placing the needle into the seal of the fluid reservoir to retain the fluid within the barrel on a second end. Configured in this manner, the seal performs a dual function of sealing the fluid in the barrel and sealing the pharmaceutical in the fluid reservoir, thereby providing an assembly separately containing the pharmaceutical and the fluid.

As shown in step 614, the method 600 may include adjusting a force applied by a stored energy mechanism of the fluid reservoir. In general, this adjustment may help to control a rate of mixing while the fluid infiltrates the barrel during use, or otherwise adjust operation of the device for improved ergonomics or mixing. While illustrated as a penultimate step in the method 600, it will be understood that this adjustment may occur at any time during fabrication or use of the device, and may be performed multiple times including one or more times during fabrication and one or more time during use by an end user.

As shown in step 616, the method may include packaging the assembly in a package for disposable single use. This may include packaging the assembly in a sterile plastic or foil packaging or the like, or this may include packaging the assembly in a multi-dose kit along with a plurality of other assemblies.

Figure 7:
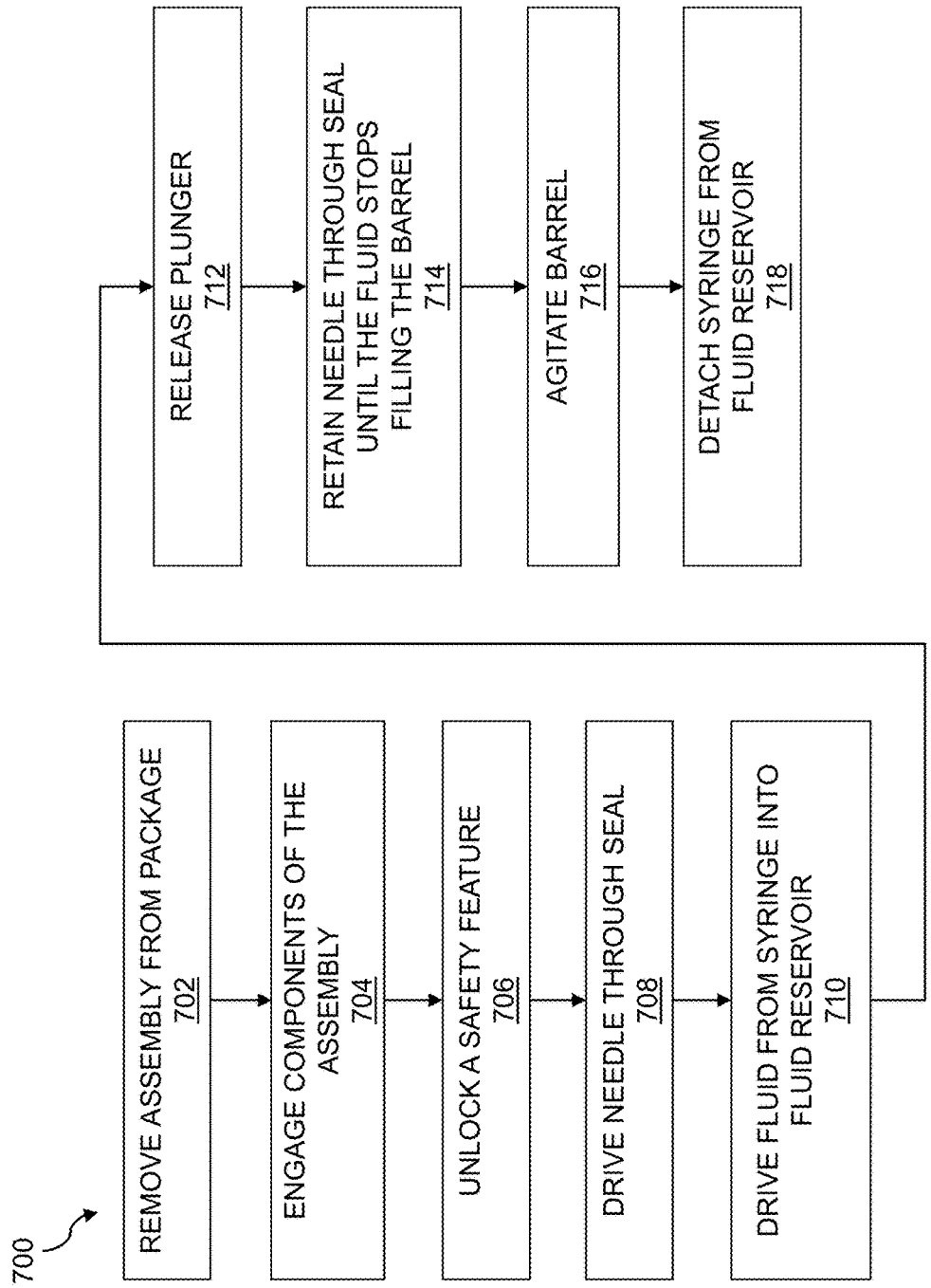
FIG. 7 is a flowchart of a method for using a device for reconstituting pharmaceuticals.

FIG. 7 is a flowchart of a method for using a device for reconstituting pharmaceuticals.

As shown in step 702, the method 700 may include removing an assembly from a package, such as any of the devices and kits described above. This may include breaking open a sterile packaging or the like that is provided for storage and shipping. As described above, the assembly may include a syringe with a needle, a reservoir with a stored energy mechanism, and a seal for the reservoir that provides a pierceable, self-sealing, leak resistant seal for contents of the fluid reservoir.

As shown in step 704, the method 700 may include engaging components of the assembly. Specifically, after the assembly is removed from the package, the components of the assembly may be configured and aligned for a reconstitution process. Aligning and configuring the components of the assembly may include, e.g., cooperating or engaging any alignment fixtures with one another, placing components into alignment fixtures, engaging safety features, and so forth.

As shown in step 706, the method 700 may include unlocking a safety feature. Specifically, after the assembly is removed from the package, the assembly may require unlocking to enable its use for reconstituting pharmaceuticals. For instance, a positional lock or the like may be moved from a locked position to an unlocked position, where one or more components of the assembly can be displaced to begin a reconstitution process.

As shown in step 708, the method 700 may include driving the needle through the seal with a plunger to couple the interior of the fluid reservoir in fluid communication with the interior of the barrel of the syringe, all as described above.

As shown in step 710, the method 700 may include driving a fluid from the syringe into the fluid reservoir with the plunger. This action pressurizes the fluid within the fluid reservoir with energy captured by the stored energy mechanism to provide a pressurized fluid within the fluid reservoir.

As shown in step 712, the method 700 may include releasing the plunger, thereby permitting the pressurized fluid to flow through the seal and needle into the barrel of the syringe.

As shown in step 714, the method 700 may include retaining the needle in a position through the seal (e.g., coupled to the interior of the fluid reservoir) until the fluid stops filling the barrel and the plunger is displaced into a ready position for use in an injection.

As shown in step 716 the method 700 may include agitating the barrel to mix the fluid and the pharmaceutical.

As shown in step 718, the method 700 may include detaching the syringe from the fluid reservoir. With properly proportioned fluid and pharmaceutical, the fluid and the pharmaceutical may combine to form a reconstituted pharmaceutical at a concentration suitable for human injection. Further, the displacement of the plunger by the stored energy mechanism may place the syringe in a state immediately ready for use in an injection. This step 718 may further include removing the syringe from any accompanying alignment fixtures or the like of the assembly as required or desired for subsequent use in injection.

Figure 8:
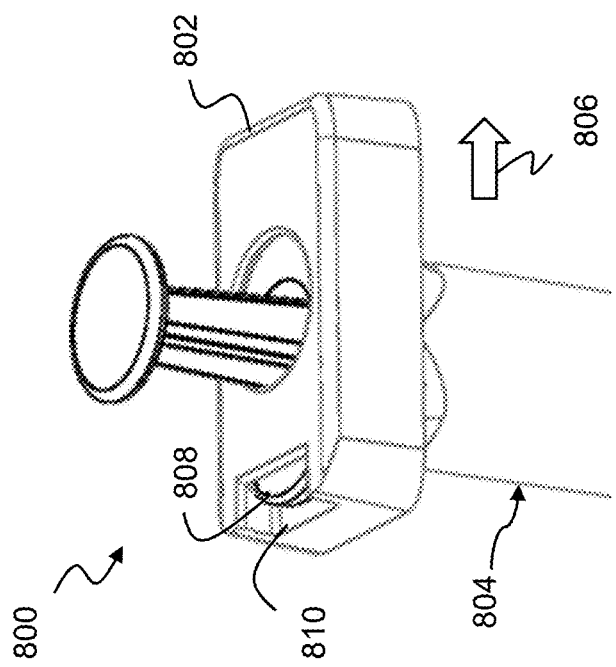
FIG. 8 shows a positional lock in a locked position.

FIG. 8 shows a positional lock in a locked position. As noted above, a device 800 for reconstituting pharmaceuticals may have a number of useful operating positions along an axis of the device, such as a first position where the open end of a needle is enclosed by a seal and a second position where the open end of the needle fully penetrates the seal to couple the interior of a barrel of a syringe in fluid communication with the interior of a fluid reservoir. A positional lock 802 or similar locking mechanism may be usefully provided to selectively secure a syringe 804 in one or more such axial positions.

More specifically, by moving the positional lock to a first position, e.g., to the right in FIG. 8 as indicated by an arrow 806, a thumb tab 808 on the syringe 804 may engage a flange 810 on the positional lock 802 and prevent axial displacement of the syringe 804 toward a fluid reservoir beyond a predetermined position established by the flange 810. Although not visible in FIG. 8, a second flange may be provided inside the positional lock 802 to engage a second thumb tab of the syringe 804 opposing the thumb tab 808 that is visible in the drawing.

Figure 9:
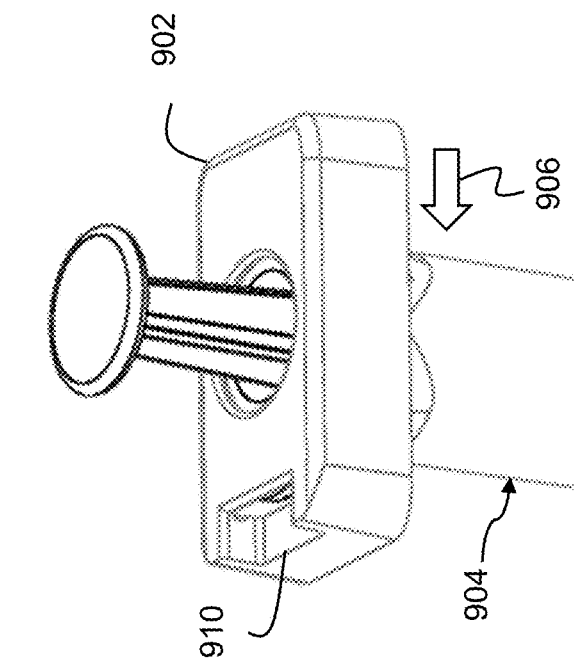
FIG. 9 shows a positional lock in an unlocked position.

FIG. 9 shows a positional lock in an unlocked position. When the positional lock 902 is moved to a second position, e.g., to the left in FIG. 9 as indicated by an arrow 906, the flange 910 may release the thumb tab and permit the syringe 904 to move toward a fluid reservoir so that the needle can penetrate a seal and couple to the interior of the fluid reservoir. It should be noted that the needle is in general rigidly fixed to the barrel of the syringe 904, and while the plunger is shown as a part of the syringe 904 in the drawing, the axial displacement of the syringe 904 controlled by the positional lock 902 include an axial displacement of the barrel and needle, which may be independent of any motion by the plunger that slides within the barrel.

It will be appreciated that the devices, systems, kits, and methods described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A device for reconstituting a pharmaceutical comprising:
   a fluid reservoir with an opening, the fluid reservoir containing a dry pharmaceutical composition;
   a seal forming a pierceable cover for the opening;
   a moving seal within the fluid reservoir, wherein the seal and the moving seal isolate the dry pharmaceutical composition in an interior of the fluid reservoir from environmental conditions;
   a stored energy mechanism configured to pressurize the interior of the fluid reservoir by applying a force to the moving seal;
   a syringe having an interior containing a fluid to reconstitute a dose of the dry pharmaceutical, wherein the seal forms a barrier between the interior of the fluid reservoir and the interior of the syringe to concurrently and separately retain the dry pharmaceutical composition in the fluid reservoir and the fluid in the interior of the syringe;
   a plunger enclosing the fluid in the interior of the syringe;
   a needle fitted to the syringe, the needle having a first and second end, the first end of the needle positioned to breach the seal opposite the fluid reservoir and the second end of the needle coupled to the interior of the syringe; and
   an alignment fixture coupled to the fluid reservoir, the alignment fixture shaped and sized to retain the needle and the syringe in a position and orientation with the needle partially breaching the seal, and the alignment fixture configured to accommodate an axial movement of the syringe to pierce the barrier with the needle and couple the interior of the fluid reservoir in fluid communication with the interior of the syringe, whereby the plunger can be depressed to first drive the needle through the pierceable cover of the seal, and then push the fluid from the syringe into the fluid reservoir.

2. The device of claim 1 wherein the moving seal includes a plunger seal sized to slide within the interior of the fluid reservoir while maintaining a fluid seal to retain the fluid within the interior of the fluid reservoir.

3. The device of claim 1 wherein the stored energy mechanism includes a mechanical spring.

4. The device of claim 1 wherein the stored energy mechanism includes a compressible fluid pressurized to apply the force to the moving seal.

5. The device of claim 1 further comprising a cap coupled to the stored energy mechanism and removably and replaceably coupled to the fluid reservoir, wherein the cap is configured to engage the stored energy mechanism with the moving seal when coupled to the fluid reservoir.

6. The device of claim 1 further comprising a liquid diluent as the fluid in the interior of the syringe.

7. The device of claim 1 further comprising a bacteriostatic solvent as the fluid in the interior of the syringe.

8. The device of claim 1 further comprising a mechanism having a first position that permits an axial displacement of the needle sufficient to pierce the seal and a second position that prevents the axial displacement of the needle from piercing the seal.

9. The device of claim 1 wherein the dry pharmaceutical composition includes a lyophilized pharmaceutical.

10. The device of claim 9 wherein the lyophilized pharmaceutical includes human chorionic gonadotropin or an immunoresponsive biologic.

11. The device of claim 1 wherein the seal is formed of a material that separates the fluid reservoir from environmental conditions.

12. The device of claim 11 wherein the seal is formed of one or more of a low-durometer rubber, a neoprene, and a polyisoprene.

* * * * *